United States Patent [19]

Menard

[11] Patent Number: 5,713,495
[45] Date of Patent: Feb. 3, 1998

[54] EYE-DROP DISPENSER GUIDE

[76] Inventor: Leslie E. Menard, 23 Highbrook Rd., Apt. 213, Bar Harbor, Me. 04609

[21] Appl. No.: 541,138

[22] Filed: Oct. 11, 1995

[51] Int. Cl.⁶ ............................................. B65D 37/00
[52] U.S. Cl. ........................ 222/212; 222/420; 604/300
[58] Field of Search ............................... 222/212, 420, 222/421, 422; 604/289, 294, 295, 300, 302

[56] References Cited

U.S. PATENT DOCUMENTS

| D. 249,709 | 9/1978 | Trovinger | 604/300 X |
|---|---|---|---|
| 4,344,430 | 8/1982 | Astrove | 604/300 |
| 4,471,890 | 9/1984 | Dougherty | 222/190 |
| 4,531,944 | 7/1985 | Bechtle | 604/302 |
| 4,605,398 | 8/1986 | Herrick | 604/300 |
| 4,960,407 | 10/1990 | Cope | 604/300 |
| 5,059,188 | 10/1991 | Goddard | 604/300 |
| 5,417,349 | 5/1995 | Stull | 222/420 |
| 5,429,621 | 7/1995 | Stahl | 222/420 X |

*Primary Examiner*—Joseph Kaufman
*Attorney, Agent, or Firm*—Chris A. Caseiro; Thomas L. Bohan

[57] ABSTRACT

An eye-drop dispenser guide designed for aiding the insertion of an eye-drop into the eye. The guide is designed to stabilize a dispenser so that an individual can safely and accurately insert drops into any area of the eye. The guide includes three essentially perpendicular regions, one designed to grasp the eye-drop dispenser, one designed to rest on the bridge of the user's nose, and one intermediate portion designed to set the eye-drop dispenser off from the user's eye. The portion that rests on the user's nose is preferably curved so as to accommodate the user's finger and to permit easy pivoting of the guide.

5 Claims, 1 Drawing Sheet

U.S. Patent     Feb. 3, 1998     5,713,495
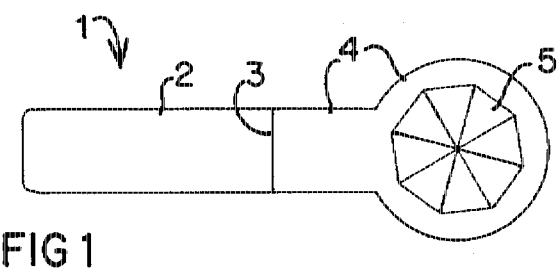
FIG 1
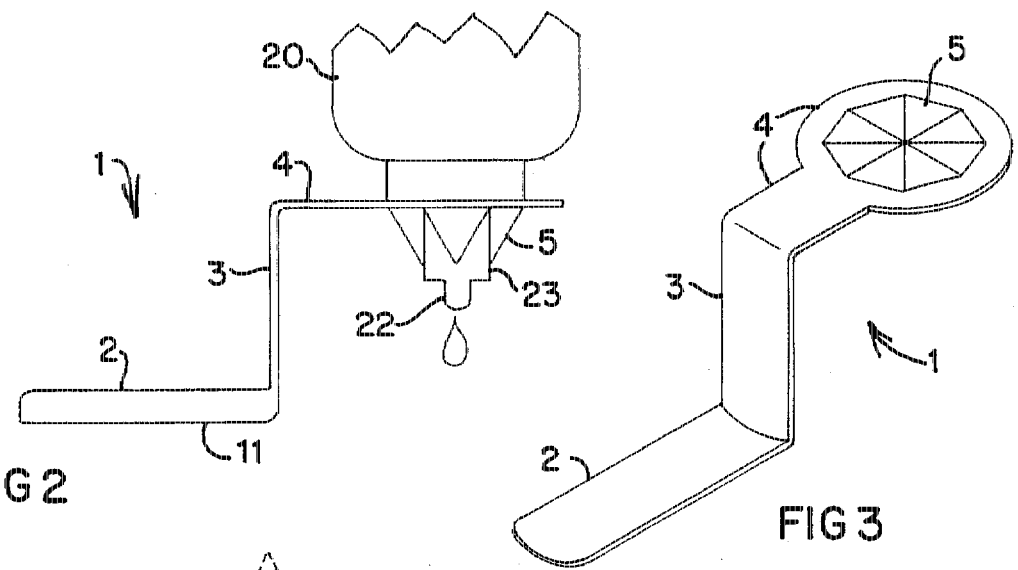
FIG 2
FIG 3
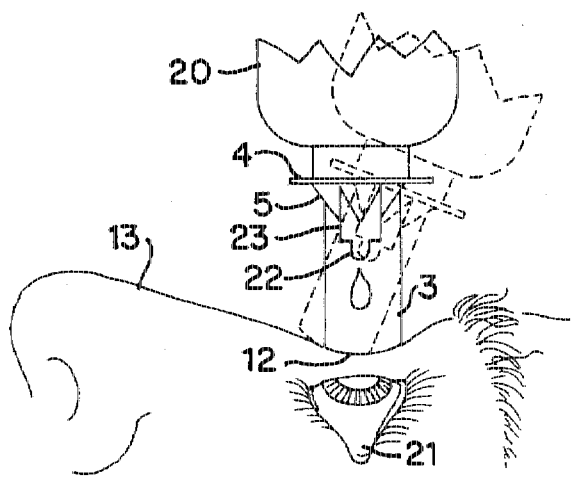
FIG 4
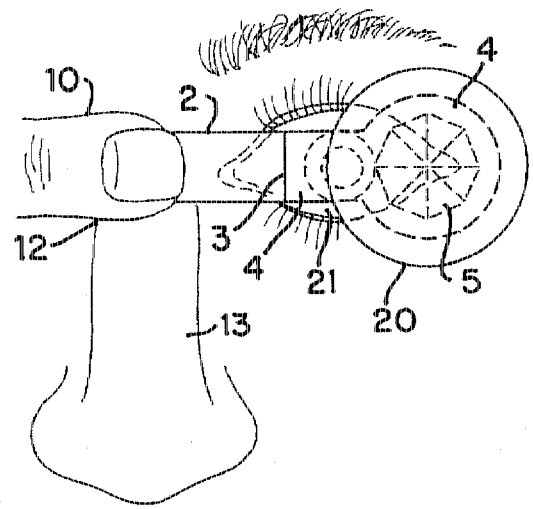
FIG 5

EYE-DROP DISPENSER GUIDE

BACKGROUND OF THE INVENTION

1. Field of the Invention

The present invention relates to a guide for aligning, stabilizing, and positioning an eye-drop dispenser when inserting eye-drops into the eye.

2. Description of the Prior Art

Inserting eye-drops, medicines, or solutions into the eye has been a longtime problem for many people. Since inserting a foreign substance into the eye is unnatural and quite unnerving, many people shake and/or blink as the drops are inserted into the eye. Aside from such nervous symptoms, another difficulty is that a significant number of people lack the strength to stabilize the dropper over the eye for the period of time required to insert the drops. It is important to accurately place the drop into the eye to avoid waste of the medicine and to ensure an easier adjustment to such a foreign substance.

Over the years, various devices have been developed to make the insertion of the drops easier. U.S. Pat. No. 4,471,890 (1984, Dougherty) teaches the use of a device for dispensing drops into the eye. The Dougherty device has an extension attached to a vial to enable the user to get the drop closer to the eye before dispensing the drops. Such a device is dangerous to use because the extension gets close to the cornea or sclera of the eye. Any shaking or movement could scratch and irritate the eye. Furthermore, this device requires that the liquid be removed from its original "sterile" vessel and placed in the dispenser. Such a process involves the unnecessary expense of providing a second vessel and also involves the risk of contamination of the liquid as the transfer to the second vessel occurs.

U.S. Pat. No. 4,531,944 (1985, Bechtle) teaches the use of an eye drop-application aid that includes a housing that covers the eye. A dropper is then inserted into the housing and aligned over the pupil by a vertical alignment indicator. This device has removable dispenser seats that conform to the various dispenser tips of common eye-drop vessels. Such a device is unnecessarily complicated and expensive to manufacture. Another problem is that this device is designed to align the dispenser tip directly over the cornea, even if that is not desired. For most people, it is easier to insert a drop onto the sclera, or white of the eye, than to insert a drop directly onto the cornea. Such a device makes it very difficult to accurately place a droplet in the corner or outer rim of the eye.

U.S. Pat. No. 5,059,188 (1991, Goddard) teaches the use of an eye drop-application aid that attaches to an eye-drop dispenser tip. Positioning of the dispenser tip is achieved by the use of an oval positioning ring to space the tip a precise distance from the side of the user's nose and the orbital rim. This device assumes that all people have similar facial structures, particularly the same dimensions from the bridge of the nose and orbital rim to the nasal canthus, and therefore that the drop will fall exactly into the nasal canthus. In order to accommodate each person's eye dimensions, various sizes and an 15 added step of measuring the individual's face would be required to insert an eye-drop in the desired region of the eye. U.S. Pat. No. 5,417,349 (1995, Stull) teaches the use of a guide for an eye-drop dispenser. This guide is basically a cap and cover designed primarily to protect against contamination. It offers no evident structural support that would facilitate the stabilization and accuracy of inserting eye-drops into the eye.

What is needed is an eye-drop dispenser guide that may be universally used with all eye-drop dispensers. What is also needed is such a guide that can be simply and inexpensively manufactured out of commonly available materials such as coated cardboard or plastic. What is further needed is such a guide that helps to stabilize a user's hand during the insertion of eye-drops into the eye. What is still further needed is such a guide that will be safe to use. What is yet further needed is such a guide that allows the user to quickly and accurately adjust the location, angle, and proximity of the dropper to the eye.

SUMMARY OF THE INVENTION

It is an object of the present invention to provide an eye-drop dispenser guide that is universal in that it can be used with most available eye-drop dispensers. Another object of the present invention is to provide such a guide that can be simply and inexpensively manufactured out of commonly available materials. Another object of the present invention is to provide such a guide that helps to stabilize the user's hand using the insertion of eye drops into the eye. Yet another object of the present invention is to provide such a guide that is safe to use. Finally, it is an object of the present invention to provide such a guide that allows the user to quickly and accurately adjust the location, angle, and proximity of the dropper to the eye.

The eye dropper guide of the present invention achieves the noted objectives by providing a structure that will support and secure common eye-drop dispensers. The present invention is designed so that the spout of the dispenser inserts into a flexible set of teeth that secure the dispenser to the guide. Various-sized spouts may be inserted into the guide regardless of whether they are threaded or smooth. This guide can be easily and inexpensively molded from a unitary piece of material such as a coated cardboard, plastic or other suitable material. The structure of this guide helps the user stabilize his or her hand by placing the guide against the bridge of the nose. This is achieved while maintaining the tip of the dispenser a reasonable distance from the eye.

In use, the eye dropper guide of the present invention is readily adjustable in order to permit the user to accurately insert a drop of fluid at any location within the eye. While holding the guide against the bridge of the nose, the user can adjust the location, angle, and proximity of the dropper to the eye. The user then squeezes the dispenser and a drop is inserted into the location desired. The guide is safe to use because it keeps the tip of the eye-drop dispenser away from the eye. Furthermore, as a result of its low manufacturing cost, it can be disposed of in order to ensure that no contamination is spread into the eye. Each eye-drop dispenser guide can be separately packaged in a sterile container.

By permitting the user to rest the guide on the nose, the device of the present invention allows weaker individuals to keep the dropper raised for a longer period of time. An advantage of the present invention is that the guide ensures that the tip of the dispenser does not touch the eye and that no contaminant from the exterior of the dispenser or from the guide is spread into the eye. Another advantage in this design is that the guide allows the user to quickly and accurately adjust the location, angle, and proximity of the dispenser tip to the eye. These and other advantages of the present invention will become apparent upon review of the drawings, detailed description of the device, and the appended claims.

BRIEF DESCRIPTION OF THE DRAWINGS

FIG. 1 is a top view of the preferred embodiment of the present invention.

FIG. 2 is a side view of the preferred embodiment of the present invention with a fluid dispenser inserted therein.

FIG. 3 is a three-dimensional view of the preferred embodiment of the present invention.

FIG. 4 is a side view of the present invention in use.

FIG. 5 is a front view of the present invention in use.

DETAILED DESCRIPTION OF THE PREFERRED EMBODIMENT

The preferred embodiment of the present invention is illustrated in FIGS. 1–5. As shown in FIGS. 1–3, an eye-drop dispenser guide I for securing an eye-drop dispenser 20 over an eye 21 includes a lower portion 2, a riser portion 3 essentially perpendicular to the lower portion 2, and an upper portion 4 essentially perpendicular to riser portion 3 and parallel to lower portion 2. In the preferred embodiment, each of these portions is approximately 1.25 inches long and 0.75 inches wide. It is to be understood that the guide 1 may be fabricated from a single piece of material such as coated cardboard wherein the three portions are folded into position. Alternatively, the guide I may be molded as a unitary body from a material such as plastic, or the like. The guide 1 may also be formed with separate pieces by attaching them together with glue or the like.

In the preferred embodiment, the lower portion 2 is curved in order to conform to the shape of a user's finger 10, as shown in FIG. 5. A lower edge 11 of the lower portion 2 is designed to be moved across a bridge 12 of the user's nose 13 in order to place the guide 1, and specifically the upper portion 4, in the desired position. The curvature of the lower portion 2 allows the user to rotate the guide I smoothly and comfortably on the badge of the nose, so that the desired angle of insertion is achieved. This allows the user to insert eye-drops from a standing, sitting, or horizontal position.

The riser portion 3 connects the lower portion 2 to the upper portion 4. The riser portion 3 secures the eye-drop dispenser 20 at a safe and comfortable distance from the eye 21 while maintaining a dispenser tip 22 close enough to provide accuracy and eliminate blinking when inserting fluid into the eye 21.

The upper portion 4 secures the eye-drop dispenser 20 within the guide 1. In the preferred embodiment, the upper portion 4 has a set of six flexible, concentrical, pie-shaped teeth 5 that grab onto a spout 23 of the eye-drop dispenser 20 as it is inserted therein. The six pie-shaped teeth 5 are formed by cutting three 0.5 inch slits in the center of the upper portion 4. Of course, it is to be understood that other means for holding the dispenser tip 22 within the upper portion 4 may be used, including, but not limited to, clip means.

FIG. 4 shows how the guide I can be easily rotated at various angles so as to give a user great flexibility in determining where to position their body prior to insertion of the fluid. FIG. 5 shows how the guide 1 is generally held by an individual while inserting the fluid. The structure of the guide 1 allows the individual to tilt the eye-drop dispenser 20 in any direction in order to insert drops in all locations of the eye 21.

The preferred embodiment of the present invention has been described herein. Further modification of the invention disclosed will occur to those skilled in the respective arts and all such modifications and equivalents are deemed to be within the scope of the invention as defined by the following claims.

What is claimed is:

1. An eye-drop dispenser guide for aligning an eye-drop dispenser over an eye of said user, said guide comprising:

a) a lower portion having a curvature conforming to a shape of a finger of said user, said curvature being sufficiently curved to provide smooth rotation of said guide on a bridge of a nose of said user;

b) a riser portion having a front side and a rear side wherein said riser portion is attached to said lower portion at a lower front end of said riser portion, said lower portion extending essentially perpendicularly from said riser portion; and c) an upper portion attached to an upper rear end of said riser portion, said upper portion extending essentially perpendicularly from said riser portion, said upper portion having means for holding said eye-drop dispenser therein;

wherein said lower portion, said riser portion, and said upper portion are substantially equal in length and arranged such that eye-drops are dispensed directly into said eye.

2. The eye-drop dispenser guide as claimed in claim 1 wherein said means for holding said eye-drop dispenser is a plurality of concentrically-aligned flexible teeth designed to bend when a tip of said eye-drop dispenser is forced therein.

3. The eye-drop dispenser guide as claimed in claim 1 wherein said guide is a unitary piece of material.

4. The eye-drop dispenser guide as claimed in claim 3 wherein said piece of material is plastic.

5. The eye-drop dispenser guide as claimed in claim 3 wherein said unitary piece of material is a coated cardboard.

* * * * *